United States Patent [19]

Falk

[11] 4,140,019
[45] Feb. 20, 1979

[54] MOLTEN METAL SAMPLER
[76] Inventor: Richard A. Falk, 519 Westminster Dr., Waukesha, Wis. 53186
[21] Appl. No.: 866,581
[22] Filed: Jan. 3, 1978
[51] Int. Cl.$^2$ .............................................. G01N 1/18
[52] U.S. Cl. ............................ 73/425.4 R; 73/DIG. 9
[58] Field of Search ..................... 73/425.4 R, DIG. 9, 73/354

[56] References Cited
U.S. PATENT DOCUMENTS
4,048,857  9/1977  Bardenheuer ................. 73/425.4 R Primary Examiner—Donald O. Woodiel
Attorney, Agent, or Firm—Henry C. Fuller

[57] ABSTRACT

A molten metal sampler employs two refractory mold halves having circular openings covered with plates to mold a disc sample and recesses communicating with the circular openings for fill passages and the formation of pin samples. The recesses in the mold halves when assembled provide integral fill and pin sample passages, a mixing chamber, deoxidant chamber, flow deflection and tortuous flow passage. The orientation of the fill passages and the recesses for the pin sample tube enable the mold to be positioned in a protective paperboard sleeve or box with one passage oriented to provide an end fill sample lance and the other passage serving as a pin sample mold. Alternatively, and in one embodiment, the pin sample mold can be employed as the fill passage by communicating through the side wall of a protective paperboard sleeve to provide a side fill immersion sampler.

12 Claims, 10 Drawing Figures

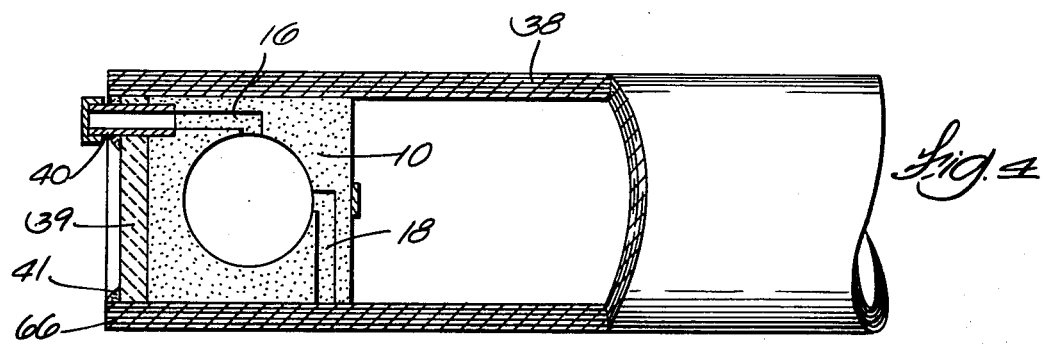
Fig. 4
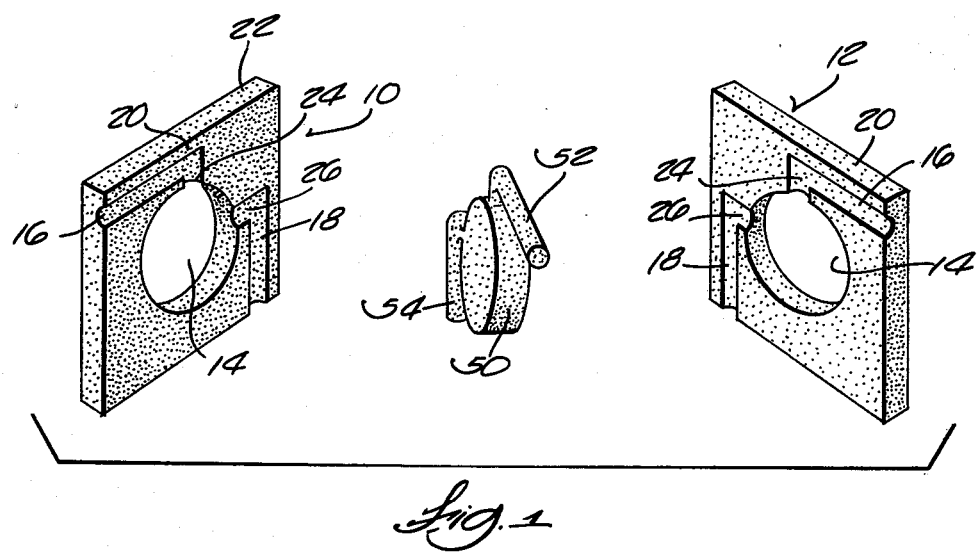
Fig. 1
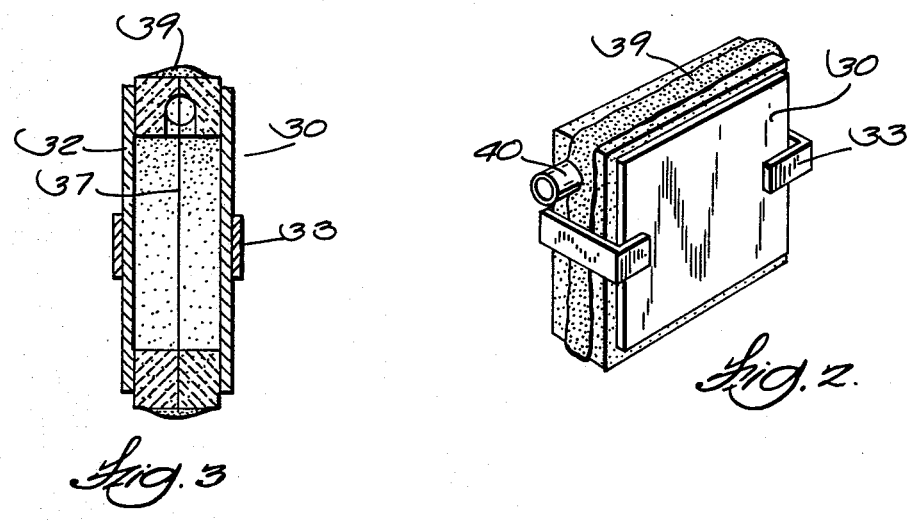
Fig. 3
Fig. 2

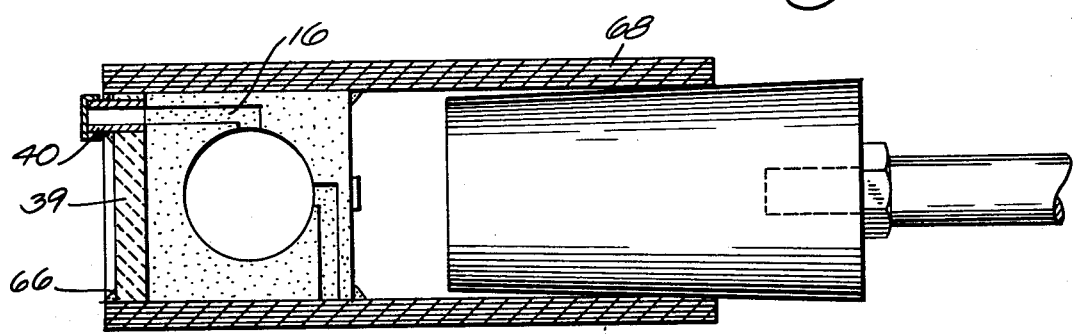
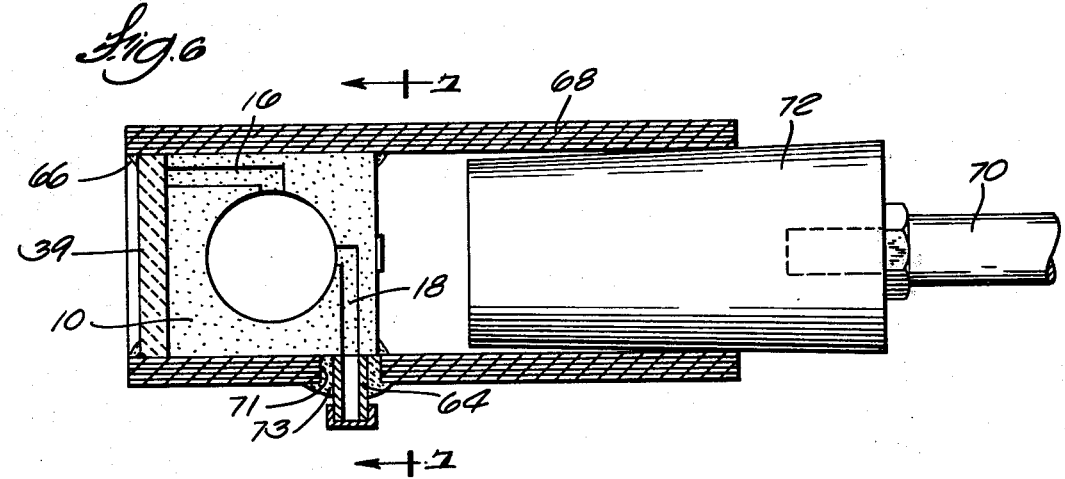
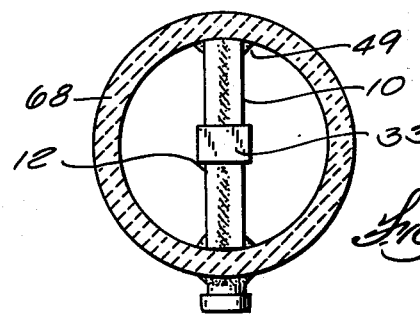

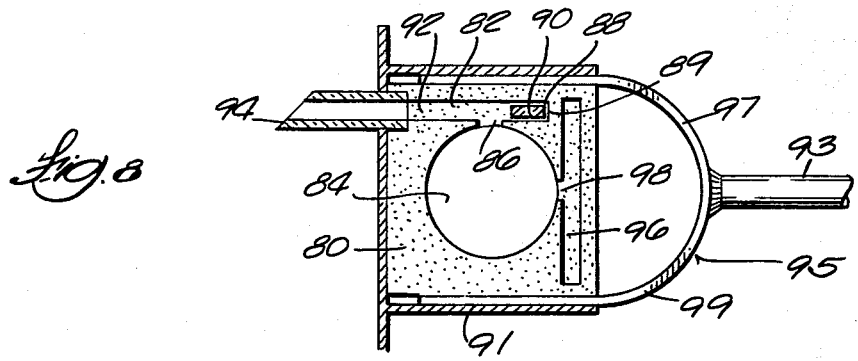
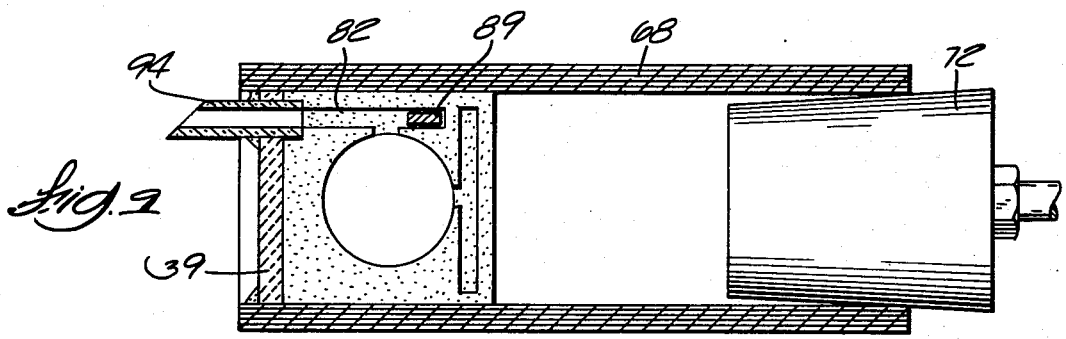
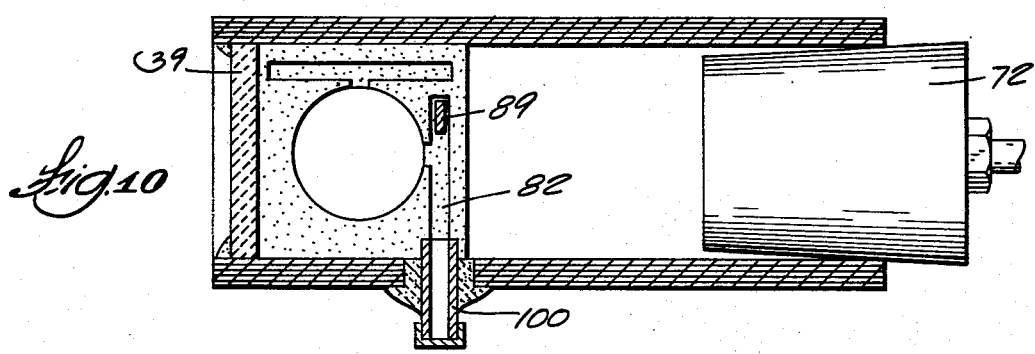

MOLTEN METAL SAMPLER

BACKGROUND OF INVENTION

My prior patent application, Ser. No. 739,217, now U.S. Pat. No. 4,069,717, discloses the use of molded refractory mold halves which are clamped together and which have central openings in each mold half with metal plates closing the openings when the mold halves are assembled together. In this patent, the pin sample passage is parallel with the fill passage and thus is not suitable for a side entry port filling as well as an end fill in a protective paperboard tube. In addition, the pin sample tube is exterior of the mold body, resulting in special assembly time and expense. For some molten metal melts, a side entry port fill passage provides better samples than an end fill sample lance because the molten metal won't run out. The present invention provides a sample mold which can be employed in end fill, side entry port samplers, stream samplers and pneumatic samplers. My prior U.S. Pat. No. 3,481,201 discloses an immersion sampler with a cylindrical refractory mold and a side entry port, and my U.S. Pat. No. 3,791,219 discloses an end fill immersion sampler.

SUMMARY OF INVENTION

The invention provides a sample mold which in one embodiment is formed from two identical mold halves which can be square in shape and which have two recesses extending along the margins of the central through openings with right angle bends in the recesses which communicate with the central openings which form the disc-shaped mold cavity. The bends in the recesses provide an abrupt change in flow direction and thus cause turbulence and a mixing function which minimizes voids in the samples and promotes good mixing of the deoxidant positioned in the fill passage or sample mold.

In one embodiment a passage aligned with the fill passage recesses and directly in the molten metal flow path provides a storage cavity for deoxidant. The storage cavity is offset from the opening into the disc cavity and hence the deoxidant is not swept or washed into the disc cavity but dissolved and thoroughly mixed with the molten metal before it enters the disc mold cavity.

The passage formed from the recesses in the mold halves which is not used as the fill passage can be plugged at the outer end to serve as the mold passage for a pin sample suitable for combustion analysis. The same mold halves with integral fill passages, mixing chambers and pin sample passages are adapted for a variety of sampling techniques including immersion sampling, stream sampling and pneumatic sampling, thus reducing the expense of manufacturing a wide variety of samplers.

The present invention provides a sampler in which all desirable functions, including elimination of sample voids, mixing of deoxidant, disc molding and pin molding are performed by recesses in the mold halves located within the outline of the integrated mold and not exteriorly thereof as with some prior art samplers.

Further objects, advantages and features of the invention will become apparent from the disclosure.

DESCRIPTION OF DRAWINGS

FIG. 1 is an exploded perspective view of the mold halves of the invention and a sample taken from the mold.

FIG. 2 is a perspective view of the assembled mold halves of the invention.

FIG. 3 is a sectional end view of the sampler shown in FIG. 2.

FIG. 4 is a fragmentary sectional view of an immersion lance embodying the mold halves of the invention.

FIG. 5 is a view similar to FIG. 4 showing the pipe and ram for manipulating the sampler which employs a short paperboard housing.

FIG. 6 is a view similar to FIG. 5 with the mold employed as a side entry port sampler.

FIG. 7 is a sectional view along line 7—7 of FIG. 6.

FIG. 8 is a side view of a modified embodiment of a sample cartridge.

FIG. 9 is a sectional view of a sampling lance embodying the sample cartridge half shown in FIG. 8.

FIG. 10 is a sectional view of a sample cartridge shown in FIG. 8 in a side fill sampler.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 discloses first and second mold halves 10 and 12 which are square in shape and provided with two through openings 14. Each mold half 10 and 12 is formed from the same mold. The mold halves 10 and 12 include recesses 16 and 18. The recesses 16 and 18 are preferably oriented at right angles and extend along the margins 20 of the mold halves between the openings 14 and the peripheral edge 22 of the mold halves. Angles other than 90° between the recesses 16 and 18 can be employed. The recesses 16 and 18 have legs 24 and 26 which are at right angles with the portions 16 and 18 and which communicate with the openings 14. The legs 24 and 26 provide a tortuous path which minimizes voids in the samples and affords good mixing of deoxidant.

When the mold halves 10 and 12 are assembled, as shown in FIGS. 2 and 3, metal or refractory closure plates 30 and 32 are employed to seal the openings 14 to form a disc-shaped mold cavity for a sample which is suitable for spectrographic analysis. Clips 33 can be employed to secure the plates 30, 32 to the refractory mold halves. The joint or split line 37 of the mold halves is desirably sealed with refractory cement 39 (FIG. 2).

In FIG. 4, the assembled mold halves are positioned in a protective elongated paperboard sleeve 38, with the recesses 16 oriented parallel to the axial direction of the sleeve 38 to provide an end fill sampler. A fused quartz tube 40 communicates with the recesses 16 to provide an entry passage into the mold cavity. The tube 40 extends through a refractory disc which is secured in place with refractory cement 41. The refractory cement 41 also seals the end of sleeve 38. The assembled mold halves can be positively positioned in the sleeve 38 with refractory cement 49 along the peripheral edge 22 between the mold and the paperboard sleeve 38 (FIG. 7). The end of passage 18 (FIG. 4) can also be plugged with refractory cement. The recesses 18 provide a mold for a pin sample tube. As shown in FIG. 1, the resulting sample comprises a disc 50 with a leg 52 and a leg 54, both of which can be used for pin samples for combustion analysis in an induction furnace.

In FIG. 6, the recesses 18 communicate with a fill tube 64 which provides a side entry port for the sample cavity. The paperboard sleeve 68 has a relatively large opening 71, and the fill tube is sealed in the opening 71 by a ring 73 of refractory cement. As in the FIG. 4 embodiment, the end of the housing 68 is sealed with a ceramic disc 39 and refractory cement 66. In FIGS. 5 and 6, the protective tube 68 is relatively short and is manipulated with a pipe 70 which is connected to a tapered plug 72 which wedges in the interior of the sleeve 68.

FIGS. 8, 9 and 10 show a modified embodiment of the invention. FIG. 8 discloses one of two allochiral mold halves 80, each of which is provided with a recess 82 which communicates with the through opening 84 via a recess or cross passage 86. The opening 84 together with the opening 84 in a second mold half 80 and closure plates 30 and 32 (not shown in FIGS. 8, 9 and 10) form the disc sample molding cavity. The recess 82 has a recess portion 88 located beyond the cross passage 86 which thus is located intermediate the length of the recess 82. The recess portion 88 terminates in a closed end 89 and provides a storage cavity for deoxidant such as aluminum 90 which is located directly in the flow path of molten metal in recesses 82. The storage cavity 88 is offset from the cross passage 86 and hence the deoxidant is not swept or washed intact into the disc molding cavity. However, because the deoxidant is located in the flow path of the incoming metal, it is dissolved and mixed prior to entry of the metal into the disc molding cavity, thus insuring uniformity in the sample. As with the other embodiments, a fused quartz fill tube 94 can be provided.

The sample mold halves 80 are also provided with pin sample recesses 96 which communicate with the sample cavity 84 by a cross passage 98 positioned intermediate the length of the pin sample recesses 96. As thus positioned, an additional tortuous path is provided to further enhance mixing of deoxidant and eliminate voids in the pin sample.

In FIG. 8, the mold halves 80 and the closure plates are contained in a cardboard box 91 which encloses the mold halves and prevents molten metal from adhering to the mold halves. The sampler in FIG. 8 is manipulated by a rod 93 which has a U-shaped fork 95 with legs 97, 99 which project into the box 91 in the gaps between the top and bottom of the mold halves and the box 91.

FIG. 9 illustrates the modified embodiment of the sample cartridge in a protective housing 68, with the passage 82 oriented for end fill. In FIG. 10 the passage 82 is oriented for side filling and communicates with a fused quartz tube 100.

The molten metal samplers of the invention provide good samples with thorough mixing of the deoxidant which provide reliable tests without any substantial voids in either the pin sample or disc sample. The samples are easily retrieved from the pin sample and sample cavities by removal of the metal plates 30, 32 from the sides of the sampler.

What is claimed is:

1. A molten metal sampler having first and second mold halves, each of said halves having peripheral edges and openings in said mold halves to define a sample cavity when said mold halves are assembled together, first and second pairs of recesses in each of said mold halves to form first and second passages, said recesses extending from said periphery into said openings to afford communication with said sample cavity, said first and second recesses of each of said mold halves being transverse, with said first passage providing a fill passage and said second passage providing a mold cavity for a pin sample, a protective housing for said mold halves, with said first passage communicating exteriorly of said housing to receive molten metal and deliver molten metal to said mold cavity and to said second passage.

2. A molten metal sampler in accordance with claim 1 wherein said protective housing has a side wall with an aperture and said first passage communicates with said aperture in said side wall of said protective housing to provide a side entry port for filling the mold cavity.

3. A molten metal sampler in accordance with claim 1 wherein said first passage communicates with the end of said housing to provide an end fill passage for filling the mold cavity.

4. A molten metal sampler in accordance with claim 1 wherein the peripheral edges of said first and second mold halves define a square and said first and second passages extend generally parallel to some of said peripheral edges.

5. A molten metal sampler in accordance with claim 1 wherein said recesses include angularly related portions which communicate with said through openings.

6. A molten metal sampler in accordance with claim 2 including an opening in said housing larger than said fill passage, a heat resistant glass fill tube located in said housing opening and communicating with said fill passage, and refractory cement arranged around said fill tube and filling and sealing said housing openings.

7. A molten metal sampler in accordance with claim 1 wherein said first passage includes a passage portion and a cross passage, said passage portion extending beyond said cross passage communicating with said first passage and communicating through said cross passage with said sample cavity at a point intermediate the length of the first passage.

8. The molten metal sampler of claim 7 wherein said passage portion of said first passage is closed and including deoxidant located in said passage portion between said cross passage and said closed end.

9. A molten metal sampler in accordance with claim 7 wherein said second passage has a cross passage for communicating with said sample cavity at a point intermediate its length.

10. A molten metal sampler including opposed refractory mold halves having recesses to define a fill passage, a box enclosing said mold halves, a fill tube extending through an opening in the box and into said fill passage, a handle, and means on said handle extending into said box between the mold halves and box walls to support the sampler on said handle and enable manipulation of the sampler.

11. A molten metal sampler having opposed refractory mold halves with openings formed from the same mold, with first and second sets of recesses at 90° so that the recesses in one half register with the recesses in the other half when one mold half is oriented at 90° with respect to the other mold half to form when assembled a fill passage with an inlet, a pin sample mold, a sample forming cavity, and cross passages connecting said first and second sets of recesses to said sample forming cavity for communication therewith, said cross passages providing a tortuous flow path to and from said sample forming cavity.

12. A molten metal sampler having opposed refractory mold halves with first and second sets of recesses to form when assembled a fill passage with an inlet, a pin sample mold, a sample forming cavity, and cross passages connecting said first and second sets of recesses to said sample forming cavity for communication therewith, said cross passages providing a tortuous flow path to and from said sample forming cavity and wherein one of said cross passages intersects said fill passage at a point intermediate the length of said fill passage to provide a storage cavity down stream from said inlet for deoxidant, and deoxidant located in said storage cavity in the path of metal flow into said fill passage.

* * * * *